United States Patent
Ward, Jr. et al.

(10) Patent No.: US 6,383,804 B1
(45) Date of Patent: May 7, 2002

(54) SAMPLING DEVICE WITH SNAP-OFF HEAD AND METHOD OF USE

(75) Inventors: N. Robert Ward, Jr., Woodinville; Geoffrey S. Bright, Bothell, both of WA (US)

(73) Assignee: International BioProducts, Inc., Bothell, WA (US)

( * ) Notice: Subject to any disclaimer, the term of this patent is extended or adjusted under 35 U.S.C. 154(b) by 44 days.

(21) Appl. No.: 09/615,185

(22) Filed: Jul. 13, 2000

(51) Int. Cl.[7] .............................. C12M 1/26; C12Q 1/24
(52) U.S. Cl. ................... 435/309.1; 435/30; 73/864.71; 600/572
(58) Field of Search .............................. 435/30, 309.1, 435/287.6; 73/864.71, 864.41; 600/572, 569; 15/209.1, 104.002, 210.1

(56) References Cited

U.S. PATENT DOCUMENTS

| | | | | |
|---|---|---|---|---|
| 885,276 | A | * | 4/1908 | McDonald |
| 3,058,139 | A | * | 10/1962 | Dryden |
| 3,508,547 | A | | 4/1970 | Deuschle |
| 3,815,580 | A | | 6/1974 | Oster |
| 4,027,658 | A | | 6/1977 | Marshall |
| 4,136,680 | A | * | 1/1979 | Southworth |
| 4,175,439 | A | | 11/1979 | Laker |
| 4,803,998 | A | * | 2/1989 | Kezes et al. |
| 4,856,136 | A | * | 8/1989 | Janssen |
| 4,934,011 | A | | 6/1990 | Haug |
| 5,341,538 | A | * | 8/1994 | Banome |
| 5,370,128 | A | | 12/1994 | Wainwright |
| 5,380,492 | A | * | 1/1995 | Seymour |
| 5,477,863 | A | | 12/1995 | Grant |
| 5,991,960 | A | * | 11/1999 | Johnson |
| 6,021,681 | A | | 2/2000 | Jezek |

* cited by examiner

Primary Examiner—William H. Beisner
(74) Attorney, Agent, or Firm—Christensen O'Connor Johnson Kindness PLLC

(57) ABSTRACT

A sampling device (10) is provided having an elongate handle (12) with a distal paddle head (14). An absorbent material (20) is placed about the paddle head, and a score line (18) is located along the handle at a location adjacent the padded head. A method of use is provided in which the paddle head (14) and absorbent material (20) are inserted into a flexible wall sample bag. The head is then grasped from the exterior of the sample bag so as to avoid direct contact with the absorbent material. The handle is then broken away from the head at the handle score line. The absorbent material (20) is preferably sized to encompass the exposed score line after the paddle head (14) is snapped from the handle (12).

17 Claims, 2 Drawing Sheets

SAMPLING DEVICE WITH SNAP-OFF HEAD AND METHOD OF USE

FIELD OF THE INVENTION

The present invention relates to applicator devices, and more particularly to a sampling device especially suited for use in sterile collection and having an applicator end of absorbent material.

BACKGROUND OF THE INVENTION

In the field of sterile collection, it is known to use swabs made of cotton, dacron or alginate to take microbiological samples. Such swabs usually include an swab stick handle that is relatively thin and somewhat bendable. After sampling, the swab is placed into a sterile test tube, plastic container, or other collection bag for transportation back to the laboratory and for later processing.

While this approach has been successful for the collection of clinical samples (e.g. throat swabs), it is less than ideal for collection of samples from floors, equipment surfaces and drains in an industrial setting, such as a food production plant. A first disadvantage is that known swabs are best suited for small sampling areas, such as a throat or body wound. Industrial surfaces are generally much larger. To account for the larger sample surface, some industrial sampling procedures use a sterile sponge that the analyst rubs across the sampling surface. The sampling sponge is held by a gloved hand or, sometimes, by sterile forceps. These sponges are effective for larger surfaces, but are susceptible to mishandling by the analyst, resulting in inaccurate results from accidental contamination of the sample.

A second disadvantage is microorganisms that colonize industrial surfaces can form strong attachments, called "biofilms", that require a certain amount of scrubbing in order to release them from their underlying surface. Consequently, it is difficult to lift this biofilm by scrubbing a wide surface area using a relatively small swab having a bendable handle.

A third drawback is that an analyst taking a sample may contaminate the sample by introducing matter from the analyst's hand onto the applicator stick (the area held by the analyst). To address issues of purity, alternative swab devices have been developed for collection of clinical samples whereby a cap holds the swab and the analyst only holds the cap. The cap also serves to seal the transport container. Such an approach does improve the purity of the sample, but unfortunately requires extra plastic and an additional manufacturing step to produce.

In addition to the above problems, a large accumulation of collection bags with sample swabs located therein is cumbersome to transport and store. Overcrowding of the bags and various types of mishandling can occur in which the swab inadvertently punctures the collection bag and, consequently, compromises the quality of the sampled content.

Thus, a need exists for an improved surface sampling device for use in sterile collection. The ideal sampling device would be easy to use and cause minimal opportunity for accidental contamination by the analyst. The device would also be effective at sampling large areas and be capable of lifting an attached biofilm through the scrubbing action by the analyst. Finally, after the sample is taken, the sampling device can be transported back to the laboratory without puncturing the bag used to transport the device. The present invention is directed to fulfilling these needs and others as described below.

SUMMARY OF THE INVENTION

In accordance with the present invention, a sampling device is provided having an elongate handle with a distal paddle head. An absorbent material is positioned about the paddle head, and a score line is located along the handle at a location adjacent the padded head. During use, the paddle head and absorbent material are snapped off of the elongate handle.

In accordance with other aspects of this invention, the absorbent material is sized to encompass the exposed score line after the paddle head is snapped from the handle. In one embodiment, the absorbent material is a single piece of generally rectangular absorbent material folded about the paddle head and adhered thereto. The head includes a distal edge and the absorbent material is folded about the distal edge. The handle and paddle head are integrally formed of a material such as polystyrene, polycarbonate, polypropylene, polyethylene, or ABS.

In one embodiment, the paddle head is approximately 0.2 cm thick, 3.2 cm wide, and 3.2 cm long; and the absorbent material is approximately 1.5 cm thick, 4.0 cm wide, and 8.0 cm long. The absorbent material overhangs the score line by an amount in the range of about 0.5 cm to about 1.0 cm, and is formed of a material such as cellulose, polyurethane, polyester, or gauze.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is a sampling device 10 for absorbing industrial chemicals, medical samples, waste material, and other such matter to be collected, transported, and later analyzed.

Figure 1:
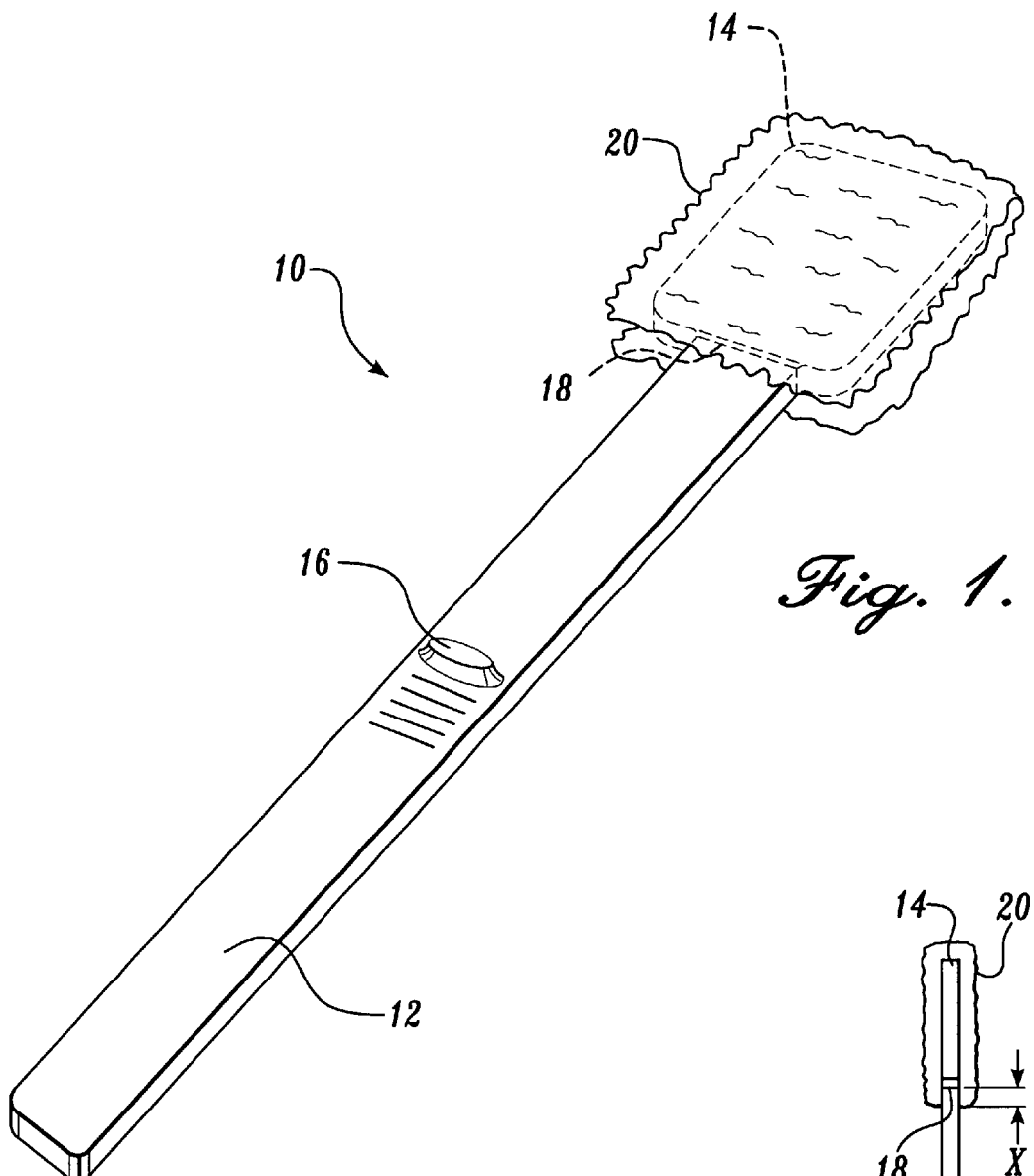
FIG. 1 is a perspective view of one embodiment of a sampling device formed in accordance with the present invention.

Referring to FIG. 1, the sampling device 10 includes an elongate handle 12 with a distal paddle head 14. The head 14 is generally flat with rounded corners, and of a width greater than the width of the handle 12. In one embodiment, the handle 12 and paddle head 14 are integrally formed of a rigid material, such as polystyrene, polycarbonate, polypropylene, polyethylene, and ABS (Acrylonitrile-Butadiene-Styrene). The handle of FIG. 1 includes a thumb stop 16 provided to improve the user's connection with the handle. The thumb stop 16 is located approximately midway along the handle length. Other types of grip-enhancing features may be used, e.g., roughened surfaces, finger indentations, etc.

A score line 18 is located along the handle at a location adjacent the padded head. A preferred score line includes first and second ends that are recessed inward. The handle portions adjacent these recessed ends are rounded so that when the paddle head is broken off (as described below)

there are no exposed sharp corners on either of the resulting handle or paddle head pieces. This arrangement reduces the risk of a user cutting themselves on the handle portion after breaking if from the paddle, and reduces the chances of a sharp corner on the paddle head poking a hole in the sterile sample bag and possibly compromising the sterility of the sample.

Figure 2:
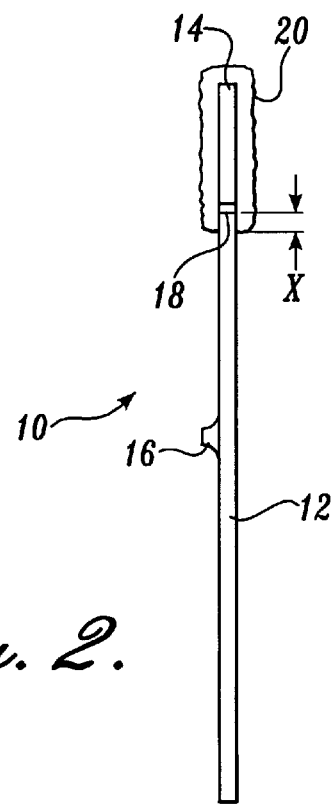
FIG. 2 is a side elevation view of the embodiment of FIG. 1.

Referring to FIGS. 1 and 2, an absorbent material 20 is placed about the paddle head in such a manner as to encompass the score line. In one embodiment, this is accomplished by sizing the absorbent material sufficiently large so as to extend past the score line by an amount X. See FIG. 2. The absorbent material is formed of an absorbent material, such as cellulose, polyurethane, polyester, or gauze.

Figure 3:
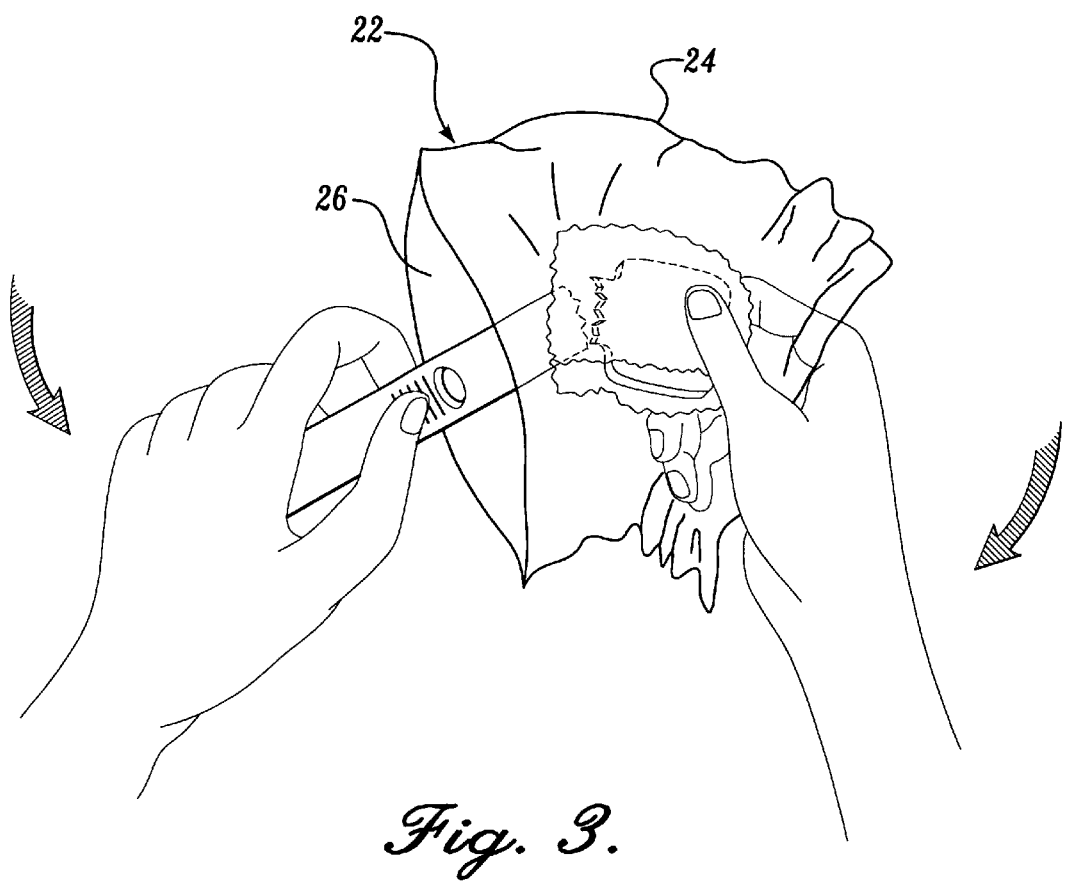
FIG. 3 is a perspective view of a preferred method of using the sampling device of FIG. 1.

In the embodiment of FIGS. 1–3, the absorbent material 20 is a single piece of generally rectangular absorbent material folded about the paddle head 14 and adhered thereto. The fold line of the material is located along the distal edge of the paddle head. The absorbent material overhangs the score line by an amount in the range of about 0.5 cm to about 1.0 cm. The paddle head 14 is approximately 0.2 cm thick, 3.2 cm wide, and 3.2 cm long; and the absorbent material is approximately 1.5 cm thick, 4.0 cm wide, and 8.0 cm long. Other arrangements are possible. For example, the fold line may be located along a side edge, or the absorbent material may be formed as a sock that slips over the paddle head.

Referring to FIG. 3, during use, a user collects the specific matter (such as microorganisms) into the absorbent material. The head and saturated material is then placed in a sterile collection bag 22 or the like. In known sterile collection bags, a flexible plastic bag body 24 includes an upper opening 26 into which the sampling device may be inserted. The user grabs the paddle head (as wrapped by the bag body) and quickly snaps the head from the handle along the score line. The score line permits this to occur with relatively little effort. The user then extracts the handle, thus leaving only the paddle head and saturated absorbent material in the sterile collection bag. This arrangement allows a user to collect a surface sample via swabbing, and deposit the sample in a sterile flexible wall container without ever directly touching the absorbent material. In one embodiment, the handle includes a thumb stop located approximately mid-way along the handle. During use, the paddle head is inserted into the sample bag up to the thumb stop.

As will be appreciated, once the handle portion is snapped away from the paddle head, the oversized absorbent material surrounds the rough edges that may exist at the score line tear points along the detached head and, thus, successfully protects the sterile collection bag from puncture. In addition, because the handle is broken off without direct contact, there is less chance of contamination by the user—both at the head and the handle.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A sampling device comprising:
   (a) an elongate handle with a distal paddle head;
   (b) an absorbent material placed about the paddle head; and
   (c) a score line located across the handle at a location adjacent the padded head; wherein during use, the paddle head and absorbent material may be snapped off of the elongate handle.

2. The sampling device according to claim 1, wherein the absorbent material is sized sufficiently large to encompass the exposed score line after the paddle head is snapped from the handle.

3. The sampling device according to claim 1, wherein the absorbent material is a single piece of generally rectangular absorbent material folded about the paddle head and adhered thereto.

4. The sampling device according to claim 3, wherein the head includes a distal edge and the absorbent material is folded about the distal edge.

5. The sampling device according to claim 4, wherein the paddle head is approximately 0.2 cm thick, 3.2 cm wide, and 3.2 cm long; and wherein the absorbent material is approximately 1.5 cm thick, 4.0 cm wide, and 8.0 cm long.

6. The sampling device according to claim 1, wherein the absorbent material overhangs the score line by an amount in the range of about 0.5 cm to about 1.0 cm.

7. The sampling device according to claim 1, wherein the absorbent material is formed of at least one of cellulose, polyurethane, polyester, and gauze.

8. The sampling device according to claim 1, wherein the handle and paddle head are integrally formed.

9. The sampling device according to claim 1, wherein the handle and paddle head are formed of at least one of polystyrene, polycarbonate, polypropylene, and acrylonitrile-butadiene-styrene.

10. The sampling device according to claim 1, wherein the handle includes a thumb stop.

11. The sampling device according to claim 1, wherein the score line ends are recessed from the edges of the handle and wherein the portions of the handle adjacent the score line ends are rounded.

12. A sampling device comprising:
   (a) an elongate handle with an integrally-formed distal paddle head, the head includes an outer edge;
   (b) a single piece of generally rectangular absorbent material folded about the paddle head outer edge and adhered thereto; and
   (c) a score line located across the handle at a location adjacent the padded head; the score line including first and second ends recessed from the edge of the handle; the portions of the handle adjacent the score line ends being rounded; the absorbent material overhanging the score line by an amount in the range of about 0.5 cm to about 1.0 cm;
   wherein during use, the paddle head and absorbent material may be snapped off of the elongate handle, the overhanging portion of the absorbent material encompassing the exposed score line after the paddle head is snapped from the handle.

13. A method of sampling microorganisms, comprising:
   (a) wiping a surface with a sampling device having an elongate handle with a distal paddle head, an absorbent material placed about the paddle head, and a score line located across the handle at a location adjacent the padded head;
   (b) inserting the paddle head with absorbent material into a flexible-walled sample bag;

(c) grasping the paddle head from the exterior of the sample bag;

(d) breaking the handle from the paddle head at the score line; and (e) removing the handle from the bag.

14. The method according to claim 13, wherein the handle includes a thumb stop located approximately mid-way along the handle; and wherein during use, the paddle head is inserted into the sample bag up to the thumb stop.

15. The method according to claim 13, wherein the ends of the score line are recessed from the edge of the handle and wherein the portions of the handle adjacent the score line ends are rounded.

16. The method according to claim 13, wherein the absorbent material is sized sufficiently large to encompass the exposed score line after the paddle head is broken from the handle.

17. The method according to claim 16, wherein the absorbent material overhangs the score line by an amount in the range of about 0.5 cm to about 1.0 cm.

* * * * *

UNITED STATES PATENT AND TRADEMARK OFFICE
CERTIFICATE OF CORRECTION

PATENT NO.      : 6,383,804 B1
DATED           : May 7, 2002
INVENTOR(S)     : N.R. Ward, Jr. et al.

It is certified that error appears in the above-identified patent and that said Letters Patent is hereby corrected as shown below:

<u>Column 4,</u>
Line 47, "padded head;" should read -- paddle head; --
Line 65, "padded head;" should read -- paddle head; --

Signed and Sealed this

Thirtieth Day of July, 2002

Attest:

Attesting Officer

JAMES E. ROGAN
*Director of the United States Patent and Trademark Office*

(12) EX PARTE REEXAMINATION CERTIFICATE (5076th)
United States Patent
Ward, Jr. et al.

(10) Number: US 6,383,804 C1
(45) Certificate Issued: Mar. 1, 2005

(54) SAMPLING DEVICE WITH SNAP-OFF HEAD AND METHOD OF USE

(75) Inventors: N. Robert Ward, Jr., Woodinville, WA (US); Geoffrey S. Bright, Bothell, WA (US)

(73) Assignee: International Bioproducts Incorporated, Bothell, WA (US)

Reexamination Request:
No. 90/006,618, May 2, 2003

Reexamination Certificate for:
| | |
|---|---|
| Patent No.: | 6,383,804 |
| Issued: | May 7, 2002 |
| Appl. No.: | 09/615,185 |
| Filed: | Jul. 13, 2000 |

Certificate of Correction issued Jul. 30, 2002.

(51) Int. Cl.[7] .............................. C12M 1/26; C12Q 1/24
(52) U.S. Cl. ................. 435/309.1; 435/30; 73/864.71; 600/572
(58) Field of Search ............................. 435/30, 309.1, 435/287.6; 73/864.71, 864.41; 600/572, 569; 15/209.1, 104.002, 210.1

(56) References Cited

U.S. PATENT DOCUMENTS

| | | | | |
|---|---|---|---|---|
| 885,276 A | * | 4/1908 | McDonald | 15/209.1 |
| 3,058,139 A | * | 10/1962 | Dryden | 15/244.1 |
| 3,508,547 A | * | 4/1970 | Deuschle | 604/1 |
| 3,815,580 A | * | 6/1974 | Oster | 600/572 |
| 4,027,658 A | * | 6/1977 | Marshall | 600/570 |
| 4,136,680 A | * | 1/1979 | Southworth | 600/572 |
| 4,175,008 A | | 11/1979 | White | |
| 4,175,439 A | | 11/1979 | Laker | |
| 4,803,998 A | * | 2/1989 | Kezes et al. | 600/572 |
| 4,856,136 A | * | 8/1989 | Janssen | 15/244.3 |
| 4,934,011 A | * | 6/1990 | Haug | 15/145 |
| 5,341,538 A | * | 8/1994 | Banome | 15/210.1 |
| 5,370,128 A | * | 12/1994 | Wainwright | 600/569 |
| 5,380,492 A | * | 1/1995 | Seymour | 422/101 |
| 5,477,863 A | * | 12/1995 | Grant | 600/572 |
| 5,991,960 A | * | 11/1999 | Johnson | 15/210.1 |
| 6,021,681 A | * | 2/2000 | Jezek | 73/864.71 |

FOREIGN PATENT DOCUMENTS

| | | |
|---|---|---|
| EP | 420 450 A1 | 4/1991 |
| GB | 2 059 992 A | 4/1981 |

\* cited by examiner

*Primary Examiner*—David Redding

(57) ABSTRACT

A sampling device (10) is provided having an elongate handle (12) with a distal paddle head (14). An absorbent material (20) is placed about the paddle head, and a score line (18) is located along the handle at a location adjacent the padded head. A method of use is provided in which the paddle head (14) and absorbent material (20) are inserted into a flexible wall sample bag. The head is then grasped from the exterior of the sample bag so as to avoid direct contact with the absorbent material. The handle is then broken away from the head at the handle score line. The absorbent material (20) is preferably sized to encompass the exposed score line after the paddle head (14) is snapped from the handle (12).

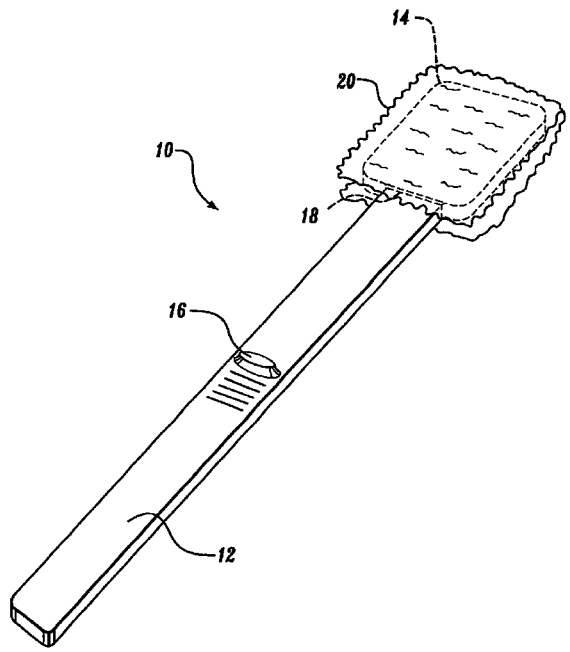

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 12 and 13 are determined to be patentable as amended.

Claims 2–11 and 14–17, dependent on an amended claim, are determined to be patentable.

1. A sampling device comprising:
    (a) an elongate handle with a distal paddle head;
    (b) an absorbent material placed about the paddle head; and
    (c) a score line located across the handle at a location [adjacent the padded head] *where a portion of the paddle head joins the handle*; wherein during use, the paddle head and absorbent material may be snapped off of the elongate handle *along the score line*.
12. A sampling device comprising:
    (a) an elongate handle with an integrally-formed distal paddle head, the head includes an outer edge;
    (b) a single piece of generally rectangular absorbent material folded about the paddle head outer edge and adhered thereto; and
    (c) a score line located across the handle at a location adjacent the paddle head; the score line including first and second ends recessed from the edge of the handle; the portions of the handle adjacent the score line ends being rounded; the absorbent material overhanging the score line by an amount in the range of about 0.5 cm to about 1.0 cm;
    wherein during use, the paddle head and absorbent material may be snapped off of the elongate handle *along the score line*, the overhanging portion of the absorbent material encompassing the exposed score line after the paddle head is snapped from the handle.
13. A method of sampling microorganisms, comprising;
    (a) wiping a surface with a sampling device having an elongate handle with a distal paddle head, an absorbent material placed about the paddle head, and a score line located across the handle at a location [adjacent the paddle head] *where a portion of the paddle head joins the handle*;
    (b) inserting the paddle head with absorbent material into a flexible-walled sample bag;
    (c) grasping the paddle head from the exterior of the sample bag;
    (d) breaking the handle from the paddle head at the score line; and
    (e) removing the handle from the bag.

* * * * *